United States Patent [19]

Eshuis et al.

[11] Patent Number: 5,721,305
[45] Date of Patent: Feb. 24, 1998

[54] POLYGLYCEROL PRODUCTION

[75] Inventors: Johan Jan W. Eshuis, Schiedam; Johannes Arie M. Laan, Breda, both of Netherlands; Glyn Roberts, Wirral, Great Britain

[73] Assignee: Unichema Chemie B.V., Gouda, Netherlands

[21] Appl. No.: 656,317

[22] PCT Filed: Nov. 30, 1994

[86] PCT No.: PCT/EP94/03978

§ 371 Date: Jun. 12, 1996

§ 102(e) Date: Jun. 12, 1996

[87] PCT Pub. No.: WO95/16723

PCT Pub. Date: Jun. 22, 1995

[30] Foreign Application Priority Data

Dec. 14, 1993 [EP] European Pat. Off. ............. 93310077

[51] Int. Cl.$^6$ .................................................. C08K 3/34
[52] U.S. Cl. .................. 524/442; 524/442; 524/445; 524/787; 524/789; 568/680; 568/619; 568/698; 549/347; 549/352; 549/353

[58] Field of Search ................................ 524/442, 445, 524/787, 789; 568/680, 619, 698; 549/347, 352, 353

[56] References Cited

U.S. PATENT DOCUMENTS 3,576,762 4/1971 Maguet-Martin et al. .
3,968,169 7/1976 Seiden et al. .
4,891,421 1/1990 Nishimura et al. .

FOREIGN PATENT DOCUMENTS 92 07795 5/1992 WIPO .

OTHER PUBLICATIONS

DATABASE WPI, Derwent Publications Ltds., AN 93-049562(06) & JP,A,5 000 981, Jan. 8, 1993, see abstract.

*Primary Examiner*—Samuel A. Acquah
*Attorney, Agent, or Firm*—Cushman Darby & Cushman IP Group Pillsbury Madison & Sutro LLP

[57] ABSTRACT

Glycerol, 2,2-dimethyl-1,3-dioxolane-4-methanol (Solketal), glycidol or glycerol carbonate is polymerized into preponderantly linear oligomers at 150° C. to 350° C. in the presence of anionic clay material, preferably hydrotalcite, as a catalyst.

12 Claims, No Drawings

POLYGLYCEROL PRODUCTION

This application claims benefit of international application PCT/EP94/03978, filed Nov. 30, 1994.

The present invention relates to a process of preparing polymers of glycerol in which glycerol or its derivatives isopropylidene glycerol (or 2,2-dimethyl-1,3-dioxolane-4-methanol), glycidol and glycerol carbonate are polymerized in the presence of a clay.

Such a process is known from Japanese Patent Application JP-A-61/238,749 (Nippon Oils and Fats Co. Ltd) in which a process has been described of manufacturing polyglycerol, with only small amounts of cyclic polymerization products. In this process glycerol is condensed after addition of 0.1–5% by weight of alkali catalyst and the same amount of an aluminium oxide comprising adsorbent. Examples of the adsorbent of the aluminium oxide type are activated alumina, zeolite, synthetic adsorbents, and also activated clays. The activated clay which has been mentioned is $V_2$ Super (ex. Mizusawa Kagaku, Japan, containing 10.4% by weight of alumina), but any further indication has not been given. The aluminium oxide type adsorbent is stated to provide a decolorizing effect during the reaction and also to exhibit a catalytic effect in that it prevents the formation of cyclic polymers of glycerol. In examples 1,2,4,5 and 7 the activated clay is used together with sodium carbonate or sodium hydroxide as the alkali catalyst. In the product compositions indicated for the examples with activated clay, the amount of cyclic polymer in the final product still ranges from 6.9 to 10.1% by weight.

In British Patent Specification GB-A-1,308,412 (Atlas Chemical Industries) crude polyglycerols are purified by contacting them with an inert, finely divided solid, such as silica, alumina, diatomaceous earth or Fullers earth at a pH of 10 to 12, after which the solid and liquid phase of the obtained slurry are separated and the liquid phase is passed throuh an anion exchange resin and subsequently through a cation exchange resin.

In our co-pending European Patent Application EP 93200356.9 (Unilever; meanwhile published as International Patent Applicatio WO-A-94/18259) we have described a process of polymerizing glycerol in the presence of an acid zeolite having an average pore size of at least 0.6 nm, in which process preponderantly cyclic polymers are formed.

It has now been found that polymers of glycerol with a high percentage of linear oligomers are obtained if glycerol or its derivatives isopropylidene glycerol (Solketal), glycidol and glycerol carbonate are polymerized in the presence of an anionic clay material.

Clay minerals are phyllosilicates, layered or two-dimensional silicates. The basic building blocks are octahedral layers of metal or non-metal oxides and hydroxides and tetrahedral layers of polymeric Si $(O, OH)_4$. In case of the generally and widely found cationic clays, interlayer alkali or alkaline earth cations and frequently water molecules, balance the excess of negative charges of the silicate sheets, which render these clays acidic. The far less common anionic clays, however, are composed of positively charged metal oxide/hydroxide layers with anions and water located interstitially. The anionic clays are also called mixed metal hydroxides since the positively charged metal hydroxides must contain two metals in different oxidation states, usually divalent and trivalent metal oxides/hydroxides, and in the sheets these share octahedral edges. Typical examples of the anionic clay minerals are hydrotalcite $(Mg_6Al_2(OH)_{16}(CO_3^{2-}).4H_2O)$, tacovite $(Ni_6Al_2(OH)_{16}(CO_3^{2-}).4H_2O$ and pyroaurite or sjogrenite $(Mg_6Fe_2(OH)_{16}(CO_3^{2-}).4H_2O)$.

The structure of hydrotalcite can exhibit wide variations in the $Mg^{2+}/Al^{3+}$ ratio, the type of anions and different divalent and trivalent cations. Anions may vary in size from small ones, such as $OH^-$ to large ones, such as $CO_3^{2-}$, and also fatty acid or dicarboxylic acid radicals, such as derived from lauric acid, stearic acid, adipic acid or dimerized fatty acids. Cations may include $Fe^{2+}$, $CO^{2+}$, $Zn^{2+}$, $Ni^{2+}$, $Cr^{3+}$, $Fe^{3+}$ and may be in admixture with $Mg^{2+}$ or $Al^{3+}$. The hydrotalcites may also be prepared synthetically, e.g. as described in United States Patent Specification U.S. Pat. No. 4,904,457 (Aluminium Corp. of America).

The advantage of the use of anionic clay, particularly hydrotalcite is that the catalyst can relatively easy be separated from the oligomeric reaction product and that the catalyst can be regenerated, e.g. by heating it while passing through an inert gas, like nitrogen. Also the crude reaction mixture obtained can directly be esterified with C2–C22 straight or branched chain monocarboxylic acids, in which esterification reaction the anionic clay also acts as a catalyst.

Therefore, the present invention relates to a process of preparing polymers of glycerol in which glycerol, 2,2-dimethyl-1,3-dioxolane-4-methanol, glycidol or glycerol carbonate is polymerized in the presence of a clay, which is characterized in that an anionic clay is used.

The anionic clay material may be a natural or a synthetic anionic clay mineral. Suitable natural materials are pyroaurite or sjogrenite, stichtite $(Mg_6Cr_2(OH)_{16}(CO_3^{2-}).4H_2O)$, reevesite $(Ni_6Fe_2(OH)_{16}(CO_3^{2-}).4 H_2O)$, eardlegite $(Ni, Zn)_6Al_2(OH)_{16}(CO_3^{2-}).4 H_2O)$, tacovite $(Ni_6Al_2(OH)_{16}(CO_3^{2-}).4 H_2O)$, meixnerite $(Mg_6Al_2(OH)_{16}(OH)_2.4H_2O)$, but also synthetic anionic clay minerals with the general formula $(ME)_{2p-x}(Me')_{2p}(OH)_{4px+4p}A_{2/n}{}^{n-}.Z\,H_2O$, in which ME is a divalent metal cation, such as Mg, Ni, Co, Zn, Cu, Me'is a trivalent metal cation, such as Al, Cr, Fe, A is a monovalent to tetravalent anion, x is from 0.5 to 8, p is from 1 to 3, n is from 1 to 4 and Z is from 0 to 10.

Preferably the anionic clay material is of the basic hydrotalcite type.

The amount of catalyst used may vary over a wide range from about 0.5% by weight to 100% by weight based on the glycerol, isopropylidene glycerol, glycidol or glycerol carbonate, but preferably from 1 wt % to 10 wt % is used.

In effecting the reaction an inert gas atmosphere may be used, such as a nitrogen blanket. The temperature at which the reaction is effected varies from 150° C. to 350° C., although also somewhat lower temperatures may be used. Preferably, a temperature of from 180° C. to 250° C. is used. A very effective method of heating is the application of microwaves. The reaction may also be favourably influenced by the application of ultrasonic vibrations. In general, by selecting the optimum reaction conditions the process according to the present invention provides polymerized glycerol having at least 50% by weight, based on the reaction mixture freed from non-polymerized glycerol, of linear oligomers of glycerol.

It has been found that when glycidol is heated to 150° C. in the presence of 0.5 to 1.0% by weight of magnesium hydrotalcite, an exothermal reaction takes place and the temperature rises to about 240° C. As a consequence of this rather violent reaction, the product obtained consisted of polyglycerol with a polymerisation degree of over 7. The determination of the hydroxyl value showed an average oligomer size of 20 to 30.

In the oligomerization of glycidol, this is therefore preferably mixed with glycerol. When glycidol was mixed with glycerol in a weight ratio of glycidol:glycerol=7:1 or 1:1, the following products were obtained (using 1% by weight of magnesium hydrotalcite and heating to 150° C.): Ratio 7:1 (results in % by weight): 17% glycerol, 8% cyclic dimer, 25% linear dimer, 3.5% cyclic trimer, 18% linear trimer, 12% linear tetramer, 8% linear pentamer, 3% linear hexamer and 5.5 higher oligomer. Ratio 1:1 (results in % by weight): 37% glycerol, 2% cyclic dimer, 31% linear dimer, 1% cyclic trimer, 16% linear trimer, 7% linear tetramer, 4% linear pentamer, 1.5% linear hexamer and 0.5% higher oligomers.

Thus it can be seen, that in case of oligomerization of glycidol it is of advantage to dilute the reaction mixture with glycerol preferably in a weight ratio of glycidol:glycerol= 1:1, but the ratio is dependent on the end result required.

In the case of glycerol carbonate as the starting material it is of advantage to start with a mixture of glycerol and diethyl carbonate. If less than the stoichiometrical amount of diethyl carbonate is used, mixtures of glycerol and glycerol carbonate in any desired composition are obtained upon heating. If these mixtures are subsequently heated with catalytic amounts of the anionic clay according to the present invention, glycerol oligomers of required composition may be obtained. Thus the oligomerization reaction can easily be controlled.

The invention will now further be illustrated on hand of the following examples.

Example 1

In a round-bottomed flask which was connected with a Dean-Stark trap to collect the water of reaction formed and which was placed in an oil bath, glycerol (300 grams) was heated to 240° C. while stirring continuously with 15 grams of hydrotalcite (Marcrosorb CT 100, Trade Mark, ex Joseph Crosfield & Sons Ltd, Warrington, UK; particle size 6–8 microns, pore size 2–50 nm). The progress of the reaction was followed by means of GLC-analysis of the silyl derivatives of samples, obtained by reacting the samples with a mixture of hexamethyldisilazane (30 parts) and trimethylsilyl chloride (15 parts) in pyridine (100 parts) prior to analysis. It turned out that after about 11 hours a conversion of 50% had been reached. The oligomeric reaction product finally obtained was diluted with water, filtered and the water was evaporated off. The results have been summarized in Table I.

Example 2

In the same way as described in Example 1, 100 grams of glycerol were polymerized in the presence of 5 grams of a synthetically prepared hydrotalcite. After 28 hrs of reaction an oligomerization product was obtained of 52% by weight of glycerol, 30% by weight of linear dimer, 11% by weight of linear trimer, 3% by weight of linear tetramer, 1% by weight of linear pentamer and less than 1% by weight of cyclic oligomers. The synthetic hydrotalcite was prepared by coprecipitation of aqueous magnesium chloride solution, aqueous sodium aluminate solution, aqueous sodium silicate solution and aqueous sodium carbonate solution (all in demineralized water) at 97° C. while stirring. After 90 minutes the mixture was filtered and washed three times with dimeralized water to a 10% by weight dispersion, which was subsequently spray-dried (inlet air temperature 220°–230° C.; outlet air temperature 110°–130° C.). The final product had a metal analysis of Mg:Al:Si=6:2.04:1.95, the average particle size was 18.0 μm, the surface area was 208 m$^2$/g (determined with BET/$N_2$ absorption method) and the intrusion volume in pores with a pore radius below 500 nm was 2.46 cm$^3$/g (as measured by mercury porosimetry).

Example 3

In the same way as described in Example 1, 100 grams of glycerol were polymerized in the presence of 10 grams of hydrotalcite (the same Macrosorb as in Example 1). After 11 hrs the composition of the oligomerization product was: 50% by weight of glycerol, 32% by weight of linear dimer, 15% by weight of linear trimer and the remainder consisted of higher linear oligomers and very small amounts of cyclic dimer and cyclic trimer.

Example 4

470 g of glycerol (5.1 moles) and 354 g of diethyl carbonate (3 moles) were heated in the presence of 4.7 g of the same Macrosorb as in Example 1. Using a Vigreux column the ethanol formed was separated, the bath temperature being 120°–130° C. After all the diethyl carbonate had reacted, which could be seen from an increasing bath temperature and a decreasing distillization of ethanol, the

| Reaction time in hrs | Glycerol monomer | Linear oligomer | | | | | Cyclic oligomer | | |
|---|---|---|---|---|---|---|---|---|---|
| | | Dimer | Trimer | Tetramer | Pentamer | Hexamer | Dimer | Trimer | Tetramer |
| 20 | 41.5 | 35.0 | 12.0 | 3.0 | 0.5 | — | 2.0 | 2.5 | 1.0 |
| 26 | 25.0 | 36.0 | 17.5 | 4.5 | 1.5 | — | 5.0 | 3.0 | 1.5 |
| 42 | 11.0 | 30.0 | 19.0 | 8.0 | 3.0 | 1.0 | 10.0 | 6.0 | 3.0 |
| 65 | 4.0 | 15.0 | 13.0 | 8.5 | 6.0 | 1.0 | 11.5 | 7.0 | 6.0 |

Composition of reaction product (wt %)

It is clear from these data that if the reaction mixture is heated too long, this leads to formation of more cyclic oliogomeric material at the cost of the linear oligomeric material. An accepted reaction time in this case appeared to be about 30 to 35 hours. The total composition of the oligomeric reaction product does not total 100% because very small amounts of higher linear and cyclic polymers have not been quantified. This effect increases with increasing polymerization time.

bath temperature was increased to 180° C. and evolution of $CO_2$ was observed. The inner temperature slowly went up to 200°–210° C. After $CO_2$ evolution had ceased the product was cooled and analysed by GLC. The composition of the product was: 39% glycerol, 1.3% cyclic dimer, 39% linear dimer, 15% linear trimer, 3.5% linear tetramer, 0.5% linear pentamer and 1.7% of higher oligomer (all percentages in % by weight).

Example 5

Glycerol carbonate was made by heating 1 eq. glycerol and 2.5 eq. diethyl carbonate in the presence of 1% by weight of Mg hydrotalcite. After all the glycerol had reacted, the excess of diethyl carbonate was distilled off. The final product was then heated at 180°–200° C. for 2 h. GLC analysis of the product at that time showed the following composition: 23% glycerol or glycerol carbonate, 7% cyclic dimer, 21% linear dimer, 20% linear dimer monocarbonate, 2% cyclic trimer, 8.5% linear trimer, 9.5% linear trimer monocarbonate, 2.7% linear tetramer, 2.6% linear tetramer monocarbonate and 3.7% of higher oligomer material (all percentages in % by weight).

We claim:

1. A process of preparing polymers of glycerol, in which glycerol, 2,2-dimethyl-1,3-dioxolane-4-methanol, glycidol or glycerol carbonate is polymerized in the presence of a clay material, characterized in that the clay material is an anionic clay material.

2. A process according to claim 1, in which the anionic clay material is selected from the group consisting of pyroaurite, hydrotalcite, tacovite, stichtite, reevesite, eardlegite, meixnerite, and mixtures thereof.

3. A process according to claim 1, in which the anionic clay material has the general formula $(Me)_{2px}(Me')_{2p}(OH)_{4px+4p}A_{2/n}^{n-}\cdot ZH_2O$ in which Me is a divalent metal cation, selected from the group consisting of Mg, Ni, Co, Zn, Cu, and mixtures thereof, Me' is a trivalent metal cation, selected from the group consisting of Al, Cr, Fe and mixtures thereof, A is a monovalent to tetravalent anion, H is 0.5 to 8, p is 1 to 3, n is 1 to 4 and Z is 0 to 10.

4. A process according to claim 1, in which the anionic clay material is a natural or synthetic hydrotalcite.

5. A process according to claim 1, in which the amount of the anionic clay is from 0.5% to 100% by weight, based on the weight of the glycerol, 2,2-dimethyl-1,3-dioxolane-4-methanol, glycidol or glycerol carbonate.

6. A process according to claim 1, in which the amount of the anionic clay is from 1% to 10% by weight, based on the weight of the glycerol, 2,2-dimethyl-1,3-dioxolane-4-methanol, glycidol or glycerol carbonate.

7. A process according to claim 1, in which a reaction temperature of from 150° C. to 350° C. is used.

8. A process according to claim 1, in which a reaction temperature of from 180° C. to 250° C. is used.

9. A process according to claim 1, in which at least 50% by weight (based on the monomer-free reaction mixture) of linear oligomers are formed.

10. A process according to claim 1, in which a starting mixture of glycidol and glycerol in a weight ratio of 1:1 is used.

11. A process according to claim 1, in which a starting mixture of glycerol carbonate and glycerol is used.

12. A process according to claim 1, in which a starting mixture of glycerol and dialkyl carbonate is used in which less than the stoichiometrical amount of dialkyl carbonate is present.

* * * * *